United States Patent
Gregory

(10) Patent No.: US 10,772,755 B2
(45) Date of Patent: Sep. 15, 2020

(54) FECAL MANAGEMENT APPLIANCE AND METHOD AND APPARATUS FOR INTRODUCING SAME

(71) Applicant: CONVATEC TECHNOLOGIES INC., Las Vegas, NV (US)

(72) Inventor: Christopher C. Gregory, Newtown, PA (US)

(73) Assignee: CONVATEC TECHNOLOGIES INC., Reno, NV (US)

(*) Notice: Subject to any disclaimer, the term of this patent is extended or adjusted under 35 U.S.C. 154(b) by 1432 days.

(21) Appl. No.: 14/451,243

(22) Filed: Aug. 4, 2014

(65) Prior Publication Data

US 2015/0005724 A1 Jan. 1, 2015

Related U.S. Application Data

(63) Continuation of application No. 13/196,375, filed on Aug. 2, 2011, now Pat. No. 8,827,970, which is a
(Continued)

(51) Int. Cl.
*A61F 5/445* (2006.01)
*A61M 3/02* (2006.01)
(Continued)

(52) U.S. Cl.
CPC .......... *A61F 5/445* (2013.01); *A61F 5/442* (2013.01); *A61M 3/0283* (2013.01);
(Continued)

(58) Field of Classification Search
CPC .......... A61M 3/0283; A61M 3/0295; A61M 25/0119; A61M 31/00; A61M 2210/1064; A61F 5/445; A61F 5/442
(Continued)

(56) References Cited

U.S. PATENT DOCUMENTS 565,386 A 8/1896 Meengs
1,026,755 A 5/1912 Birger
(Continued)

FOREIGN PATENT DOCUMENTS

CN 2174997 8/1994
CN 2325054 6/1999
(Continued)

OTHER PUBLICATIONS

Allen et al., Manometric Measurement of Anal Canal Resting Tone—Comparison of a Rectosphinteric Balloon Probe with a Water-Perfused Catheter Assembly, Digestive Diseases and Sciences, vol. 43, No. 7 (Jul. 1998), pp. 1411-1415.
(Continued)

*Primary Examiner* — Andrew J Mensh
(74) *Attorney, Agent, or Firm* — Taft Stettinius & Hollister LLP; Ryan O. White

(57) ABSTRACT

The end of the elongated tubular element of the appliance that is designed to be inserted into a body cavity is formed entirely of soft, compliant material. That end carries an inflatable balloon made of non-expandable material, formed in the fully inflated shape, to prevent overexpansion. The balloon is inflated to a predetermined low pressure level to prevent pressure necrosis in the adjacent tissue. A method and apparatus for introducing the soft end of the appliance into the body cavity are also provided. The introducer apparatus includes rigid core surrounded by a soft, compliant sleeve. The sleeve extends beyond the rigid core to form an invertable section. The soft end of the appliance is situated adjacent the apparatus, the balloon is wrapped around the apparatus, and the sleeve section is inverted over the appliance, compressing the balloon and forming a soft, rounded insertion tip. The unit is then introduced into the
(Continued)

body cavity. After the appliance is separated from the apparatus, the apparatus is withdrawn.

20 Claims, 6 Drawing Sheets

Related U.S. Application Data continuation of application No. 10/929,136, filed on Aug. 28, 2004, now Pat. No. 8,016,816.

(60) Provisional application No. 60/501,218, filed on Sep. 9, 2003.

(51) Int. Cl.
*A61F 5/442* (2006.01)
*A61M 25/01* (2006.01)
*A61M 31/00* (2006.01)

(52) U.S. Cl.
CPC ....... *A61M 3/0295* (2013.01); *A61M 25/0119* (2013.01); *A61M 31/00* (2013.01); *A61M 2210/1064* (2013.01)

(58) Field of Classification Search
USPC ........................................................ 604/317
See application file for complete search history.

(56) References Cited

U.S. PATENT DOCUMENTS

| | | |
|---|---|---|
| 2,457,244 A | 12/1948 | Lamson |
| 2,494,393 A | 1/1950 | Lamson |
| 2,813,531 A | 11/1957 | Cannula |
| 3,459,175 A | 8/1969 | Miller |
| 3,487,837 A | 1/1970 | Petersen |
| 3,509,884 A | 5/1970 | Bell |
| 3,543,744 A | 12/1970 | LePar |
| 3,548,828 A | 12/1970 | Vasile |
| 3,734,100 A | 5/1973 | Walker et al. |
| 3,766,920 A | 10/1973 | Greene |
| 3,802,418 A | 4/1974 | Clayton |
| 3,884,242 A | 5/1975 | Bazelt et al. |
| 3,937,224 A | 2/1976 | Uecker |
| 3,938,521 A | 2/1976 | Ritota et al. |
| 3,983,879 A | 10/1976 | Todd |
| 4,013,077 A | 3/1977 | Ritota et al. |
| 4,019,515 A | 4/1977 | Kornblum et al. |
| 4,030,500 A | 6/1977 | Ronnquist |
| 4,067,335 A | 1/1978 | Silvanov |
| 4,117,847 A | 10/1978 | Clayton |
| 4,121,589 A | 10/1978 | McDonnell |
| 4,182,332 A | 1/1980 | Delaney |
| 4,285,341 A | 8/1981 | Pollack |
| 4,344,434 A | 8/1982 | Robertson |
| 4,368,739 A | 1/1983 | Nelson, Jr. |
| 4,403,982 A | 9/1983 | Clayton |
| 4,471,782 A | 9/1984 | Shuffield |
| 4,496,356 A | 1/1985 | Lognion |
| 4,516,578 A | 5/1985 | Shuffield |
| 4,583,983 A | 4/1986 | Einhorn et al. |
| 4,596,554 A | 6/1986 | Dastgeer |
| 4,637,814 A | 1/1987 | Leiboff |
| 4,662,890 A | 5/1987 | Burton |
| 4,676,778 A | 6/1987 | Nelson, Jr. |
| 4,686,985 A | 8/1987 | Lottick |
| 4,721,508 A | 1/1988 | Burton |
| 4,750,488 A | 6/1988 | Wuchinich et al. |
| 4,750,902 A | 6/1988 | Wuchinich et al. |
| 4,826,481 A | 5/1989 | Sacks et al. |
| 4,988,822 A | 1/1991 | Anderson |
| 5,041,100 A | 8/1991 | Rowland et al. |
| 5,053,023 A | 10/1991 | Martin |
| 5,057,073 A | 10/1991 | Martin |
| 5,080,650 A | 1/1992 | Hirsch et al. |
| 5,160,330 A | 11/1992 | Cross |
| 5,171,305 A | 12/1992 | Schickling |
| 5,257,981 A | 11/1993 | Takahashi |
| 5,261,898 A | 11/1993 | Polin et al. |
| 5,279,596 A | 1/1994 | Castaneda et al. |
| 5,295,984 A | 3/1994 | Contente et al. |
| 5,342,321 A | 8/1994 | Potter |
| 5,356,399 A | 10/1994 | Takahashi |
| 5,404,881 A | 4/1995 | Cathaud et al. |
| 5,421,827 A | 6/1995 | Temple |
| 5,423,764 A | 6/1995 | Fry |
| 5,429,626 A | 7/1995 | Fenton |
| 5,496,296 A | 3/1996 | Holmberg |
| 5,520,669 A | 5/1996 | Mulholland |
| 5,545,149 A | 8/1996 | Brin et al. |
| 5,569,216 A | 10/1996 | Kim |
| 5,569,218 A | 10/1996 | Berg |
| 5,603,698 A | 2/1997 | Roberts et al. |
| 5,632,271 A | 5/1997 | Brain |
| 5,654,054 A * | 8/1997 | Tropsha ................ B01L 3/5082 206/524.2 |
| 5,674,197 A | 10/1997 | van Muiden et al. |
| 5,693,036 A | 12/1997 | Kilgour |
| 5,697,365 A | 12/1997 | Pell |
| 5,722,965 A | 3/1998 | Kuczynski |
| 5,766,209 A | 6/1998 | Devonec |
| 5,782,745 A | 7/1998 | Benderev |
| 5,785,641 A | 7/1998 | Davis |
| 5,791,036 A | 8/1998 | Goodin et al. |
| 5,807,314 A | 9/1998 | Ross et al. |
| 5,845,125 A | 12/1998 | Nishimura et al. |
| 5,860,952 A | 1/1999 | Quinn |
| 5,897,537 A | 4/1999 | Berg et al. |
| 5,904,701 A | 5/1999 | Daneshvar |
| 5,906,605 A | 5/1999 | Coxum |
| 5,911,715 A | 6/1999 | Berg et al. |
| 5,941,860 A | 8/1999 | Wheeler |
| 5,964,732 A | 10/1999 | Willard |
| 5,971,967 A | 10/1999 | Willard |
| 5,984,964 A | 11/1999 | Roberts et al. |
| 5,997,546 A | 12/1999 | Foster et al. |
| 6,171,295 B1 | 1/2001 | Garabedian et al. |
| 6,217,565 B1 | 4/2001 | Cohen |
| 6,240,231 B1 | 5/2001 | Ferrara et al. |
| 6,254,570 B1 | 7/2001 | Rutner et al. |
| 6,286,555 B1 | 9/2001 | Pauker et al. |
| 6,296,631 B2 | 10/2001 | Chow |
| 6,342,052 B1 | 1/2002 | Allende |
| 6,406,453 B1 | 6/2002 | Goode et al. |
| 6,413,228 B1 | 7/2002 | Hung et al. |
| 6,468,245 B2 | 10/2002 | Alexandersen |
| 6,527,755 B1 | 3/2003 | Salama |
| 6,575,934 B2 | 6/2003 | Duchamp |
| 6,585,705 B1 | 7/2003 | Maginot et al. |
| 6,635,047 B2 | 10/2003 | Forsberg |
| 6,663,614 B1 | 12/2003 | Carter |
| 6,698,428 B2 | 3/2004 | Brain |
| 6,716,209 B2 | 4/2004 | Leiboff |
| 6,719,709 B2 | 4/2004 | Whalen et al. |
| 6,723,084 B1 | 4/2004 | Maginot et al. |
| 6,743,218 B2 | 6/2004 | Maginot et al. |
| 6,743,219 B2 | 6/2004 | Dwyer et al. |
| 6,758,857 B2 | 7/2004 | Cioanta et al. |
| 6,769,116 B1 | 7/2004 | Sexton |
| 6,814,718 B2 | 11/2004 | McGuckin, Jr. et al. |
| 6,855,137 B2 | 2/2005 | Bon |
| 6,881,209 B2 | 4/2005 | Boatman et al. |
| 6,960,163 B2 | 11/2005 | Ewers et al. |
| 7,008,412 B2 | 3/2006 | Maginot |
| 7,025,557 B2 | 4/2006 | Japikse et al. |
| 7,025,757 B2 | 4/2006 | Reilly et al. |
| 7,029,467 B2 | 4/2006 | Currier et al. |
| 7,077,841 B2 | 7/2006 | Geiser et al. |
| 7,122,025 B1 | 10/2006 | Nestenborg |
| 7,147,627 B2 | 12/2006 | Kim et al. |
| 7,156,100 B1 | 1/2007 | Brain |
| 7,390,322 B2 | 6/2008 | McGuckin, Jr. et al. |
| 7,526,754 B2 | 4/2009 | Bentolila |

(56) References Cited

U.S. PATENT DOCUMENTS

| | | | |
|---|---|---|---|
| 7,722,583 | B2 | 5/2010 | Kim et al. |
| 7,735,069 | B2 | 6/2010 | Bustelo et al. |
| 8,016,816 | B2 | 9/2011 | Gregory |
| 8,827,970 | B2 | 9/2014 | Gregory |
| 2002/0016607 | A1 | 2/2002 | Bonadio et al. |
| 2002/0173771 | A1 | 11/2002 | Dono |
| 2003/0105485 | A1 | 6/2003 | Balceta et al. |
| 2003/0195490 | A1* | 10/2003 | Boatman ............ A61L 29/06 604/525 |
| 2003/0208223 | A1* | 11/2003 | Kleiner ............ A61B 1/00151 606/198 |
| 2004/0030380 | A1 | 2/2004 | Shulze et al. |
| 2004/0039348 | A1 | 2/2004 | Kim et al. |
| 2006/0122709 | A1 | 6/2006 | Devonec |
| 2009/0030386 | A1 | 1/2009 | Kim et al. |
| 2009/0030387 | A1 | 1/2009 | Kim et al. |
| 2009/0149824 | A1 | 6/2009 | Kim et al. |
| 2010/0229159 | A1 | 9/2010 | Odaira et al. |

FOREIGN PATENT DOCUMENTS

| | | |
|---|---|---|
| CN | 2489797 | 5/2002 |
| DE | 24 47 996 | 4/1976 |
| DE | 4436796 A1 | 4/1996 |
| EP | 0109897 | 5/1984 |
| EP | 0246176 A2 | 11/1987 |
| EP | 0274415 A2 | 7/1988 |
| EP | 0282449 A1 | 9/1988 |
| EP | 0793951 A1 | 9/1997 |
| EP | 0913165 | 5/1999 |
| EP | 1514572 A2 | 3/2005 |
| FR | 2326208 | 4/1977 |
| FR | 2660561 | 10/1991 |
| GB | 1026755 A | 4/1966 |
| GB | 1522391 | 8/1978 |
| GB | 2224212 | 5/1990 |
| GB | 2243553 A | 11/1991 |
| JP | 51-123399 | 10/1976 |
| JP | 62-281955 A | 12/1987 |
| JP | 63-164956 | 7/1988 |
| JP | 63-164957 | 7/1988 |
| JP | 2255155 | 10/1990 |
| JP | 3-71301 | 3/1991 |
| JP | 3-91357 | 9/1991 |
| JP | 6-197977 | 7/1994 |
| JP | 6-210002 | 8/1994 |
| JP | 3019990 | 1/1996 |
| JP | 8-66477 | 3/1996 |
| JP | 8-509394 | 10/1996 |
| JP | 9-094296 | 4/1997 |
| JP | 9507151 | 7/1997 |
| JP | 9-253112 | 9/1997 |
| JP | 10-179750 | 7/1998 |
| JP | 10-234854 | 9/1998 |
| JP | 10-305057 | 11/1998 |
| JP | P2001-536 A | 1/2000 |
| JP | 2000-167041 | 6/2000 |
| JP | 2000-354634 | 12/2000 |
| JP | 2002-126094 | 5/2002 |
| JP | 2002-153564 | 5/2002 |
| KR | 960005818 | 5/1996 |
| WO | WO8000414 | 3/1980 |
| WO | WO9108013 | 6/1991 |
| WO | WO9217219 | 10/1992 |
| WO | WO-9638106 A1 | 12/1996 |
| WO | WO9728840 | 8/1997 |
| WO | WO9743987 | 11/1997 |
| WO | WO9833458 | 8/1998 |
| WO | WO9833535 | 8/1998 |
| WO | WO0113829 | 3/2001 |
| WO | WO0149224 | 7/2001 |
| WO | WO01083017 | 11/2001 |
| WO | WO0226293 | 4/2002 |
| WO | WO03086507 | 10/2003 |
| WO | WO-2004018022 A1 | 3/2004 |

OTHER PUBLICATIONS

Australian Office Action, dated Apr. 11, 2008 (3 pages).
Blair et al., The Bowel Management Tube: An Effective Means for Controlling Fecal Incontinence, Jnl. of Pediatric Surgery, vol. 27, Issue 10, Oct. 1992, pp. 1269-1272.
Christensen et al, Neurogenic colorectal dysfunction—use of new antegrade and retrograde colonic wash-out methods. International Medical Soc'y of Paraplegia, Spinal Cord, Apr. 2000 38(4):255-261.
Di Lorenzo, C., Chronic Constipation and Fecal Incontinence in Children with Neurological and Neuromuscular Handicap. Journal of Pediatric Gastroenterology & Nutrition, 25:37-39 (1997).
European Examination Report, EP 03705823, dated Apr. 8, 2009 (4 pages).
Grogan et al., The Rectal Trumpet Use of a Nasopharyngeal Airway to Contain Fecal Incontinence in Critically Ill Patients. Jnl. of Wound, Ostomy and Continence Nursing: vol. 29, Issue 4, pp. 193-201, Jul. 2002.
Japanese Office Action, dated Jun. 10, 2008, from Japan Patent Application No. 2004-530762 (with translation).
Kim and Shin, Poster Abstract, "Clinical Application of a Continent Anal Plug in Bed-Ridden Patients with Intractable Diarrhea" Diseases of the Colon & Rectum, May 2000, vol. 43, No. 5, cover, index, and p. A49.
Kim et al., "Clinical Application of Continent Anal Plug in Bed-Ridden Patient with Intractable Diarrhea" (with translation). Jnl. of the Korean Soc'y of Coloproctology, 16 (3), 2000.
Kim et al., "Passive Bowel Movement Effects Using a New Colostomy Device: An Acute Experiment on a Dog" (with translation). Jnl. of the Korean Soc'y. of Colo Proctology, 14(3).
Kim, M.D., et al. "Clinical Application of a Continent Anal Plug in Bedridden Patients with Intractable Diarrhea" Dis Colon Rectum, vol. 44(8):1162-1167 (Aug. 2001).
Kosorak, Colostomy Tube: New Device for a Continent Colostomy, Dis. Colon Rectum, vol. 38(7): Jul. 1995.
Letter from K.H. Shin of Yushin Medical Co., Ltd. To Serjeants, UK, dated Sep. 24, 2009 indicating mailing of samples, which samples Applicant believes to be the same as a Zassi BMS 4CM submitted to the USPTO in this application in a separate Information Disclosure Statement.
Lim, Kim and Shin. "Application of a New Colostomy Device in Incontinent Dog Model" (with translation). Jnl. of the Korean Soc'y of Coloproctology, 14(3) (presented at the 16th conference of the ISUCRS, held in Malmo, Sweden in 1998).
Mathers et al., Anal Sphincter Dysfunction in Parkinson's Disease, Archives of Neurology, 46(10), Oct. 1989.
Moore et al., Problem Solving and Troubleshooting: The Indwelling Catheter. Jnl. of Wound, Ostomy and Continence Nurses Soc., 1995.
Nakamura et al., Research on Functionalization of Enema Catheter, Ikigaku, 69(10) (1999).
Paulo, M.D. et al., The Procon Incontinence Device: A New Nonsurgical Approach to Preventing Episodes of Fecal Incontinence. The American Journal of Gastroenterology, 97(9):2328-32 (Mar. 26, 2004) (Work presented at Digestive Disease Week, Atlanta, GA, May 20-23, 2001).
PCT Patent Application No. PCT/US03/01594, International Search Report.
Peiia, Bowel Management for Fecal Incontinence in Patients With Anorectal Malformations, Pediatric Surg., 33(1):133-7, Jan. 1998.
Pemberton et al., A Continent Ileostomy Device, Ann. Surg., 197(5):618-26, May 1983.
Peritoneal Dialysis Access and Exit-Site Care Including Surgical Aspects, Twardowski, Z.J., et al., Chap. 9, Textbook of Peritoneal Dialysis, 2nd Ed., Kluwer Academic Publishers, Dordrecht, The Netherlands, 2000 (pp. 317-362).

(56) References Cited

OTHER PUBLICATIONS

Photographing Technique to Achieve Good Double Contrast Film of a Complex Sigmoid Colon in an Enema Procedure, Akira Ogawa: Mejiro NT Building Clinic, Therapeutic Research, vol. 13, suppl. 2, 1992.
Photographs of a device, which device Applicant believes to be a Zassi BMS 4CM, and which device was made by Zassi Medical, which is owned by Hollister Inc., 2000 Hollister Drive, Libertyville, IL 60048, which device was submitted in an Opposition proceeding against European Patent Application No. 20040021323, photographs taken by Julie Mays on or about Dec. 9, 2010.
Problems in Wet Colostomy Management Following Radical Pelvic Surgery—Use of a New Giant Balloon Catheter, Amer. Jnl. of Surgery, Sep. 1952, p. 378.
Read, N.W., et al., Why do patients with faecal impaction have faecal incontinence. Gut, 27:283-287 (1986).
Shandling et al., The Enema Continence Catheter in Spina Bifida: Successful Bowel Management. J. Pediatr. Surg., 22(3):271-3, Mar. 1987.
Slide Presentation, Clinical application of a new colostomy device, IMSOP, Denmark, 1999.
Tsuruoka Masanori, Technique of a Disposable Barium Enema Examination Device. Therapeutic Research vol. 13, suppl. 2, 1992.
U.S. Appl. No. 10/929,136 Office Action dated Aug. 30, 2007.
U.S. Appl. No. 10/929,136 Office Action dated Dec. 10, 2008.
U.S. Appl. No. 10/929,136 Office Action dated Jan. 16, 2008.
U.S. Appl. No. 10/929,136 Office Action dated Jul. 14, 2008.
U.S. Appl. No. 10/929,136 Office Action dated Jun. 9, 2009.
U.S. Appl. No. 10/929,136 Office Action dated Nov. 15, 2006.
U.S Appl. No. 10/929,136 Office Action dated Oct. 26, 2009.
U.S. Appl. No. 10/929,136 Office Action dated Apr. 30, 2010.
U.S. Appl. No. 13/196,375 Office Action dated Aug. 12, 2013.
U.S. Appl. No. 13/196,375 Office Action dated Feb. 20, 2014.
U.S. Appl. No. 11/553,731 Office Action dated Jun. 22, 2009.
Umeda Kazuo et al., New Double Balloon Catheter for Enema Examination. Image Information Medical, 24(21), Oct. 1992.
A Unique system designed to protect patients and practitioners from fecal contact and contamination. Zassi Medical Evolutions—Bowel Management System. 2003. 10 pages.
Boretos et al., Concise Guide to Biomedical Polymers. Their Design, Fabrication and Molding. Springfield, IL., Charles C. Thomas Publishers, 1973, 18 pages.
Bristol-Myers Squibb Company, Response to the Summons to Attend Oral Proceedings, Apr. 4, 2011, 3 pages.
Bristol-Myers Squibb Company, Written Statement Setting Out the Grounds of Appeal, Sep. 22, 2011, 4 pages.
Convatec Technologies Inc., Response to the Preliminary Opinion of the Opposition Division, Feb. 19, 2015, 30 pages.
Convatec Technologies Inc., Response to the Preliminary Opinion of the Opposition Division, Sep. 8, 2016, 30 pages.
Decision of the Technical Board of Appeals 3.2.08, dated Oct. 10, 2013, 9 pages.
Dictionary of Composite Materials Technology, Stuart M. Lee, editor. 6 pages, 1989.
Echols et al., Initial experience with a new system for the control and containment of fecal output for the protection of patients in a large burn center. Annual Meeting of the John A. Boswick, MD Burn and Wound Care Symposium, Feb. 2004, 2 pages (abstract).
Hollister Incorporated, Written Statement Setting Out the Grounds of Appeal, Jan. 27, 2012, 15 pages.
Notice of Opposition to a European Patent, EP Patent No. 1514572, Sep. 3, 2009, 5 pages,
Revocation of the European Patent, European Patent No. 1514572, May 17, 2011, 18 pages.
Summons to Attend Oral Proceedings for EP Application No. 04021323.3, dated Dec. 10, 2015, 15 pages.
Summons to Attend Oral Proceedings for EP Application No. 04021323.3, dated Jun. 2, 2014, 14 pages.
Summons to Attend Oral Proceedings for European Patent Application No. 04021323.3, dated Oct. 17, 2016, 12 pages.
Webster's New Encyclopedic Dictionary, 5 pages, 1993.
Zassi Medical Evolutions, Bowel Management System, pamphlet, 6 pages, 2002.
Third Party Observations, dated Aug. 9, 2013, 6 pages.
Hollister Incorporated, Written Submissions in Response to the Summons to Attend Oral Proceedings dated Feb. 26, 2013, sent Sep. 10, 2013, 4 pages.
Bristol-Myers Squibb Company, Observations in Response to the Observations by the Third Party, dated Sep. 26, 2013, 8 pages.
European Patent Application No. 08167258.6 Communication dated May 3, 2017.
European Patent Application No. 1514572 Written Submission filed Jul. 21, 2017, 15 pages.

* cited by examiner

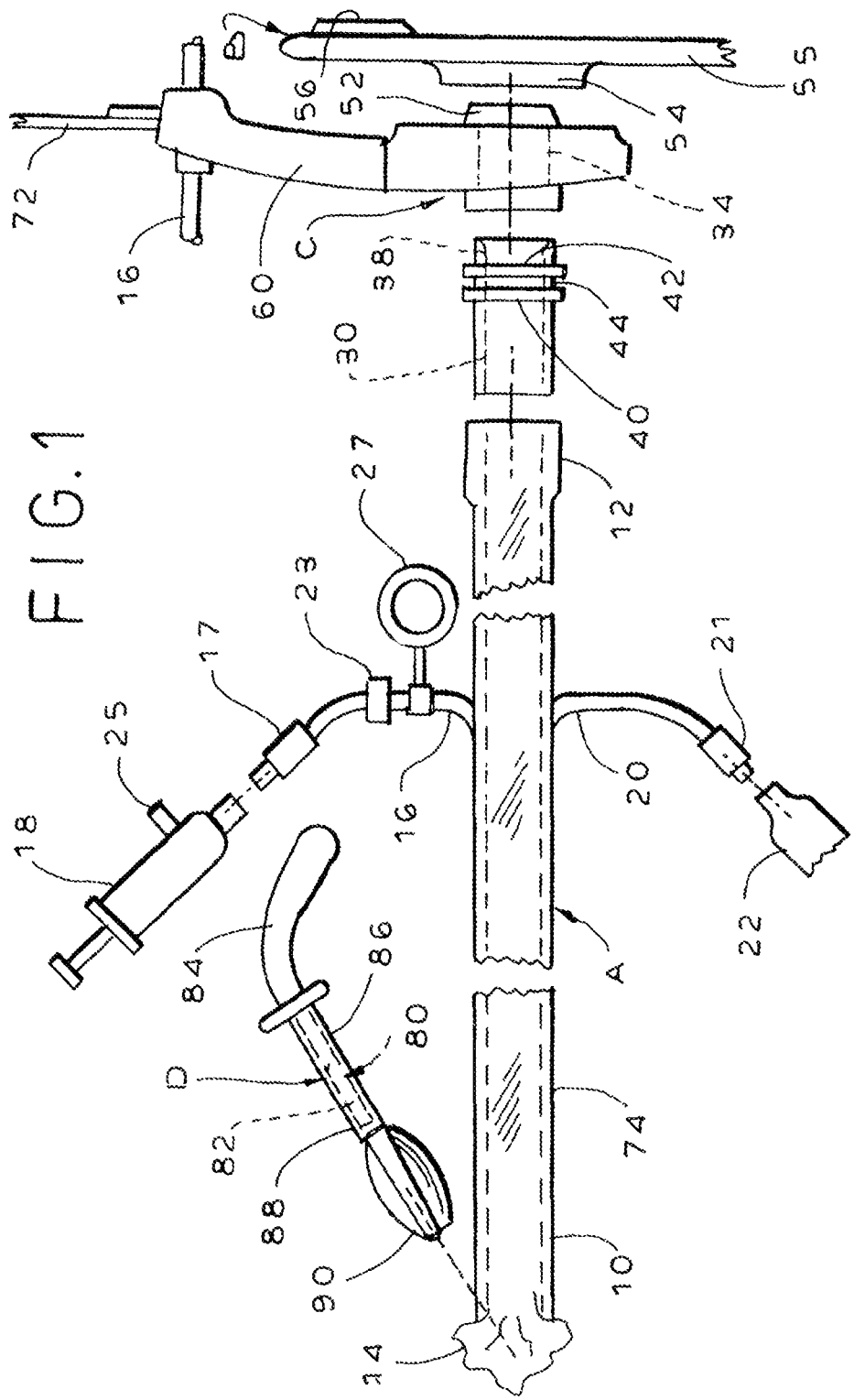

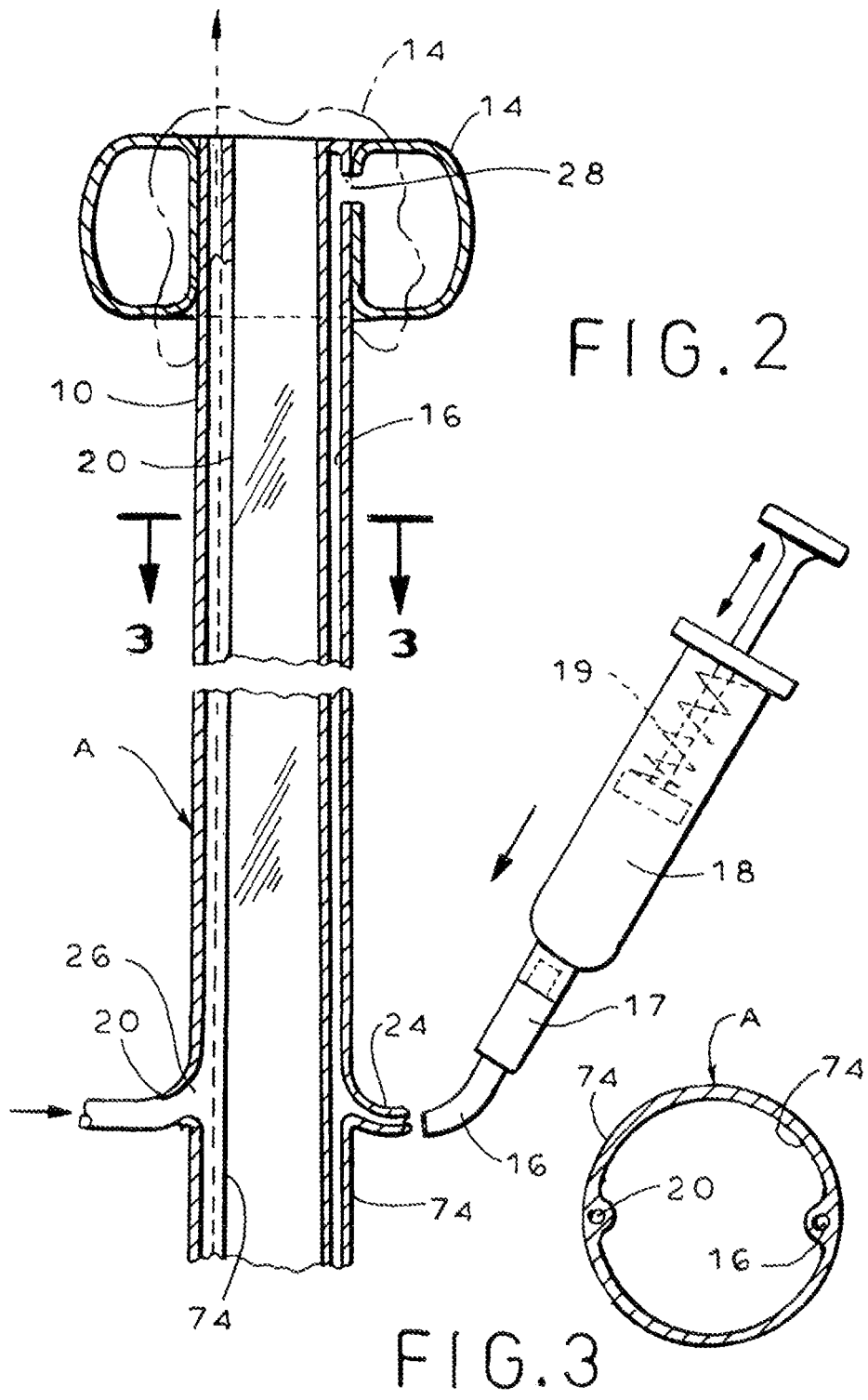

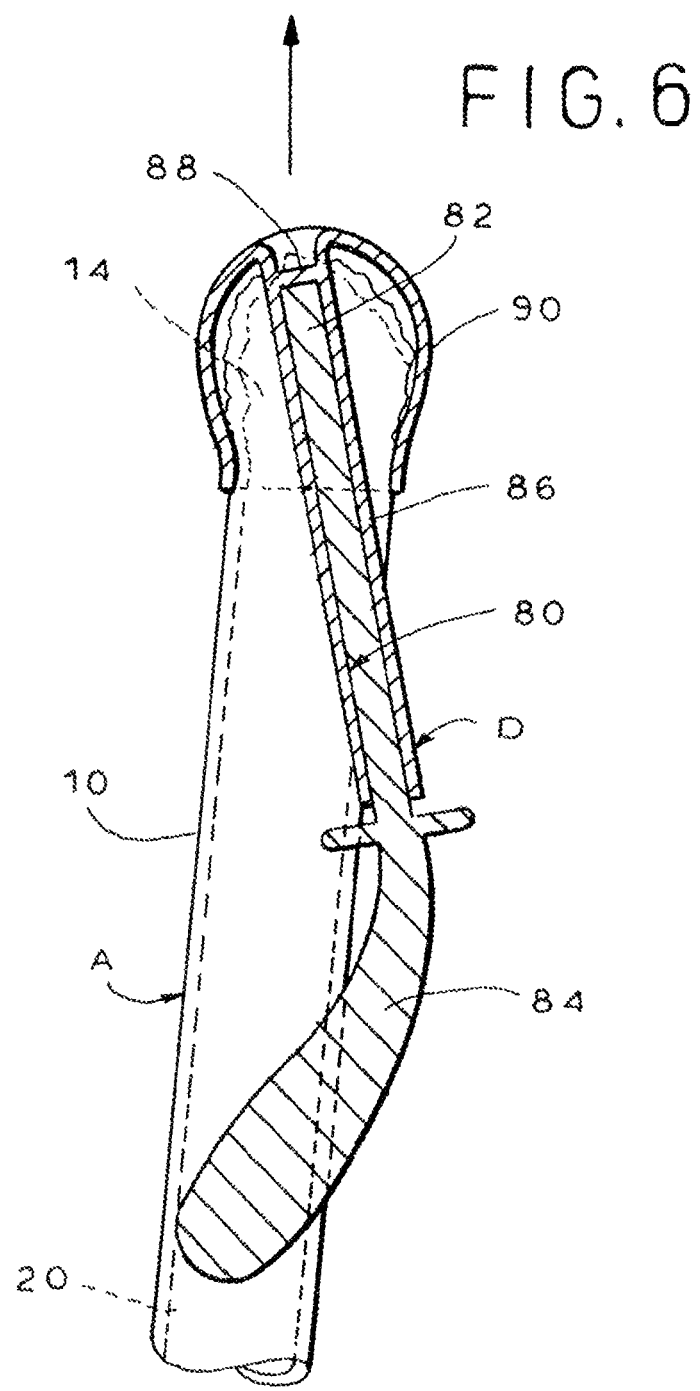

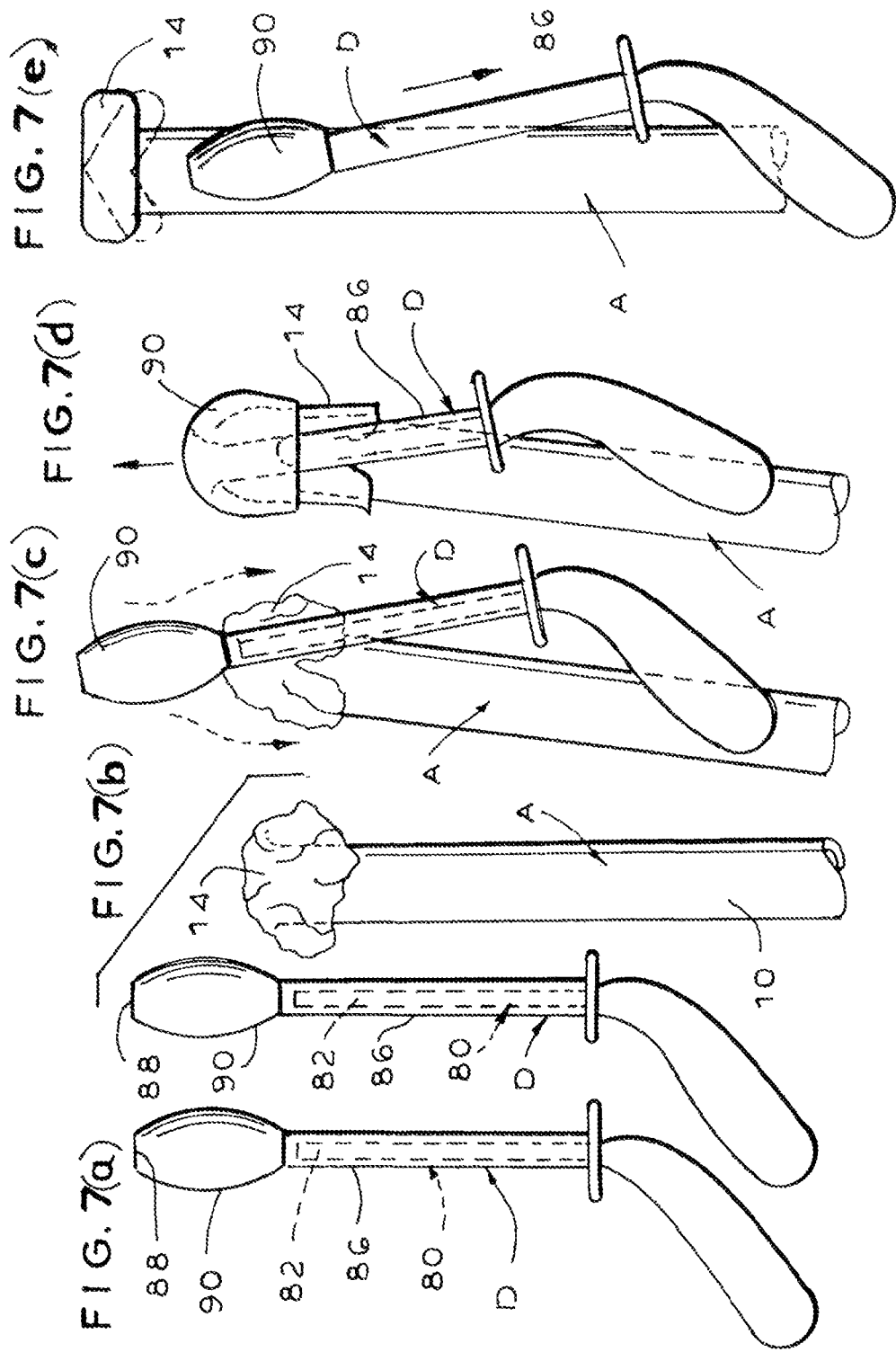

FECAL MANAGEMENT APPLIANCE AND METHOD AND APPARATUS FOR INTRODUCING SAME

CROSS-REFERENCE TO RELATED APPLICATIONS

This is a continuation of application Ser. No. 10/929,136, filed Aug. 28, 2004, which application was based on Provisional Application Ser. No. 60/501,218, filed Sep. 9, 2003, and priority on those applications is hereby claimed.

STATEMENT REGARDING FEDERALLY SPONSORED RESEARCH OR DEVELOPMENT

Not Applicable

REFERENCE TO A "SEQUENCE LISTING", A TABLE, OR A COMPUTER PROGRAM LISTING APPENDIX SUBMITTED ON COMPACT DISC

Not Applicable

BACKGROUND OF THE INVENTION

1. Field of the Invention

The present invention relates to a fecal management appliance, and to a method and apparatus for introducing the appliance into a body cavity, and more particularly to a fecal management appliance including a tubular element with a balloon carrying distal end formed entirely of soft, compliant material, that includes integral inflation and irrigation lumens, and has a detachable collection receptacle rotatably connected to its proximal end, and to a method and a separate apparatus for introducing the distal end of appliance into a body cavity.

Contamination by fecal matter of open wounds, burns, sutured surgical incisions and the like located proximate the rectum or stoma may be extremely detrimental to patient recovery. Further, healthcare professionals that accidentally come in contact with such waste while caring for patients with those conditions, many of which have severe medical problems requiring intense care, may unintentionally spread infectious diseases.

Accordingly, it is highly desirable to have a system for the management and collection of bowel contents that effectively prevents contamination of the patient and of the healthcare workers providing care to the patient.

2. Description of Prior Art Including Information Disclosed Under 37 CFR 1.97 and 1.98

One such system designed to provide bowel management is marketed by Zassi Medical Evolutions, Inc. of Fernandina Beach, Fla. 32034. The Zassi system consists of an elongated flexible catheter, the proximal end of which is detachably connected to a waste collection bag. The distal end of the catheter is designed to be inserted through the rectum or stoma into the bowel of the patient.

The distal end of the Zassi catheter includes a rigid portion to permit insertion and positioning of the catheter into the bowel. The catheter carries two inflatable balloons, one balloon being situated within the other balloon. The balloons are separately inflatable to block the distal end of the catheter and to seal the catheter to the rectum or stoma, respectively. A separate inflation lumen is provided for each balloon. A third lumen delivers irrigation fluid to the bowel.

Dual balloon systems of this type are known and are disclosed in U.S. Pat. No. 5,569,216 issued Oct. 29, 1996 to Kim, entitled "Multipurpose Colostomy Device Having Balloons On An End Thereof" and in International Publication Number WO 02/26293, published Apr. 4, 2002, and entitled "Improved Colostomy Device."

Aside from the complexity and cost of the dual balloon system utilized in the Zassi bowel management system, the Zassi apparatus has other drawbacks. Those drawbacks relate to the rigidity of the distal end of the catheter and to the pressure exerted by the balloons upon the adjacent tissue, during and after inflation.

Balloons located on the exterior of the distal end of catheters have been used for many years to hold the catheters in place in a patient's rectum. Such catheter systems are frequently used for enema application but are also used for the collection and directing of fecal material from the rectum to a collection system. Those catheters, sometimes known as Foley catheters, are large versions of devices commonly used for urinary catheterization.

There are many professionals in the medical community who do not approve of the use of inflatable devices in the rectum, as they believe that tissue damage will result from excess pressure exerted on adjacent tissue by the inflated balloon for an extended time. Such tissue necrosis is known to occur when the pressure from the balloon prevents the tissue from being sufficiently profused by blood.

In practice, after the catheter is inserted into the rectum, the balloon is inflated to its full size, regardless of the pressure that it exerts on tissue. Thus, the size of the balloon selected becomes critical. However, since the caregiver has no knowledge of the internal anatomy of the patient, the choice of balloon size is no more than a guess.

The Zassi bowel management system suffers from both of those problems. The distal end of the catheter has a rigid portion to permit insertion and therefore can cause soft tissue damage. The balloon system can be inflated to a pressure that results in prevention of the tissue from being sufficiently profused by blood.

BRIEF SUMMARY OF THE INVENTION

The present invention is a medical appliance for fecal management that overcomes both of those drawbacks. The distal end of the appliance is formed entirely of soft, compliant material, incapable of causing any injury to the tissue. The appliance utilizes a single low pressure balloon that cannot exert excess pressure on the adjacent tissue and hence cannot prevent the adjacent tissue from being profused by blood.

My invention transfers the rigid portion of a distal end of the appliance needed for insertion to a separate apparatus, designed to be withdrawn after introduction of the appliance in the bowel, thus allowing the entire inserted distal end of the appliance to be soft and compliant so that it cannot damage the tissue. The introducer apparatus includes a rigid core element surrounded by a soft, compliant sleeve. The soft sleeve is attached to the rigid core element, allowing the two to function as a unit. A section of sleeve extends beyond the end of the rigid core element. The sleeve is pinched off or crimped at a point adjacent the distal end of the core element to maintain its position relative to the element. The proximal end of the sleeve is preferably attached at the proximal end of the core element.

The soft end of the appliance to be inserted in the body cavity is wrapped around the introducer apparatus, flush with the end of the apparatus. The sleeve section that extends beyond the core element is inverted back over portion of the end of the appliance that is wrapped around the apparatus.

The inverted sleeve section acts to compress the end of the appliance and contains the compressed appliance end. This results in a smooth, rounded, compressed mass at the tip of the introducer apparatus that facilitates insertion.

The compressed appliance end is introduced into the body cavity by pushing the distal end of the rigid introducer apparatus through the anal sphincter or stoma. The rigid core element is manipulated by the proximal end until the appliance is positioned as desired. The soft end of the appliance, wrapped around the apparatus, is compressed significantly by both the constriction of the inverted sleeve section and the force of the anatomy squeezing the distal end of the introducer apparatus Once in position, the appliance and the introducer apparatus are separated. The exposed portion of the appliance is held firmly while the introducer apparatus is pushed in the distal direction. This pushes the inverted sleeve section off the end of the appliance, separating the appliance from the apparatus. Alternatively, if the appliance has a balloon structure in it, the appliance and the introducer apparatus can be separated by the inflating of the balloon. Once the appliance and the introducer apparatus are separated, the introducer apparatus is withdrawn from the body cavity, leaving the distal end of the appliance in place.

With regard to the damage potentially caused by a balloon inflated to a high pressure, my invention allows the use of a balloon catheter in the rectum with drastically reduced potential for tissue damage due to pressure necrosis. After insertion, the balloon in my device can be inflated only to a pressure that is known to be low enough to allow full profusion of the tissue. Due to force balance, the balloon can therefore apply no more than this pressure to the tissue, always permitting full profusion of the tissue. Further, the balloon is fabricated of non-expandable material, in its fully inflated shape. As a consequence, the balloon cannot expand to a harmful size.

In accordance with one aspect of the present invention, a fecal management appliance is provided. The appliance includes an elongated tubular element having a distal end and a proximal end. An inflatable balloon surrounds the distal element end of the tubular element. An externally accessible inflation lumen is operably connected to the balloon. A fecal collection receptacle is provided. Means are provided for detachably mounting the receptacle to the proximal end of the element. The distal end of the element is formed entirely of soft, compliant material.

Preferably, the distal end of the element is formed of silicone. The balloon is also formed entirely of soft, compliant material. That material could be silicone, as well.

Preferably, the balloon is substantially toroidal in shape when fully inflated. Means are provided for inflating the balloon to a pre-determined minimal pressure. Those means include means for supplying inflation fluid to the inflation lumen. The inflation fluid supply means may include a syringe with a plunger and a spring. A pressure gauge and a valve may be included to prevent over inflation.

The balloon is formed in its fully inflated size and shape. It is formed of substantially non-expandable material, so that it cannot expand beyond a predetermined size.

The tubular element includes a wall. At least a portion of the inflation lumen is attached to the wall. The wall has an interior surface. At least a portion of the inflation lumen is integral with the interior wall surface. The wall has an opening through which the inflation lumen extends.

An externally accessible irrigation lumen may also be provided. The irrigation lumen has an end proximate the edge of the distal end of the element. At least a portion of the irrigation lumen is integral with the wall of the element. Preferably, at least a portion of the irrigation lumen is attached to the interior wall surface. The wall has an opening through which the irrigation lumen extends.

Preferably, the inflation lumen extends substantially the entire length of the element. The irrigation lumen also preferably extends substantially the entire length of the element.

Preferably, the inflation lumen is attached to the wall, along substantially the entire length thereof. The irrigation lumen is also preferably attached to the interior wall surface, along substantially the entire length of the element.

The inflation lumen has a section situated within the element and a section external to the element. The irrigation lumen also has a section situated within the element and a second external to the element.

The appliance further comprises means for supplying irrigation fluid to the irrigation lumen. The irrigation fluid supply means may include a syringe.

The receptacle mounting means includes a plate with an opening. Means are provided for attaching the proximal end of the tubular element to the plate, in alignment with a plate opening. Those attaching means include means for permitting rotation of the proximal end of the tubular element relative to the plate. The rotation permitting means include a first part adapted to receive the proximal end of the tubular element and a second part mounted to the plate. The first part is rotatably mounted to the second part.

The plate includes means for retaining the external inflation lumen section. The plate further includes means for retaining the external irrigation lumen section.

The appliance is designed for use with a stationary member, such as a bed rail or the like. It includes means for attaching the plate to the stationary member.

The means for detachably mounting the collection receptacle to the plate includes first and second inter-engagable coupling parts. The first part is fixed to the plate, surrounding the plate opening. The receptacle has a wall with an opening. The second part is fixed to the receptacle wall, surrounding the wall opening.

Since the end of the appliance adapted to be introduced into a body cavity is made entirely of soft, compliant material, apparatus for introducing the apparatus, separate from the appliance, is provided. The introducer apparatus includes a substantially rigid elongated core having a distal end and a proximal end, and a sleeve having a distal end and a proximal end. The core is received within the sleeve, with a section of the sleeve extending beyond the distal end of the core.

The extended sleeve section is invertible to engage the distal end of the tubular element of the appliance. The section of the distal end of the sleeve that extends beyond the distal end of the core has a crimp therein, proximate the distal end of the core. Preferably, the invertable sleeve section is formed of soft, compliant material.

Preferably, the proximal end of the sleeve is attached to the proximal end of the core. This permits the appliance and the apparatus to function as a unit.

In accordance with another aspect of the present invention, apparatus for introducing a medical appliance into a body cavity is provided. The apparatus includes a substantially rigid elongated core having a distal end and a proximal end, and a sleeve having a distal end and a proximal end. The core is received within the sleeve. A section of the distal end of the sleeve extends beyond the distal end of the core. That section is invertable to engage the medical appliance.

The section of the distal end of the sleeve that extends beyond the core has a crimp wherein, proximate the distal end of the core. That section of the distal end of the sleeve is formed of soft, compliant material.

Preferably, the proximal end of the sleeve is attached to the proximal end of the shaft.

In accordance with another aspect of the present invention, a method is provided for introducing the soft end of a medical appliance into a body cavity utilizing introducer apparatus. The apparatus has a substantially rigid elongated core received within a sleeve, with a section of the sleeve extending beyond the core. The method includes the steps of placing the distal end of the medical appliance adjacent the apparatus, proximate the sleeve section. The sleeve section is then inverted over the distal end of the medical appliance, to engage the medical appliance. The distal end of the core, with the inverted sleeve section engaging the appliance, is introduced into the body cavity. The apparatus is then separated from the appliance and withdrawn from the body cavity, leaving the appliance in place.

The method further includes the step of wrapping the distal end of the medical appliance around the apparatus, before inverting the sleeve section.

The method further includes the step of crimping the sleeve at a point proximate the distal end of the core, to define the invertable sleeve section.

The medical appliance may include an inflatable balloon at the distal end. In that case, the method further includes the step of inflating the balloon after the end of the apparatus with the inverted sleeve section engaging the medical appliance is introduced into the body cavity. This causes the inverted sleeve section to return to its non-inverted position, disengaging the medical appliance.

BRIEF DESCRIPTION OF THE SEVERAL VIEWS OF THE DRAWINGS

To these and to such other objects which may hereinafter appear, the present invention relates to a fecal management appliance, and to a method and apparatus for introducing the end of the appliance into a body cavity, as set forth in detail in the following specification, and recited in the annexed claims, taken together with the accompanying drawings, wherein like numerals refer to like parts, and in which:

FIG. 1 is an exploded plan view of the parts of the medical appliance and introducer apparatus of the present invention;

FIG. 2 is a cross-sectional view of the distal end of the medical appliance;

FIG. 3 is a cross-sectional view taken along line 3-3 of FIG. 2;

FIG. 6 is a cross-sectional view of the distal end of the medical appliance engaged by the introducer apparatus; and FIGS. 7(a) through 7(e) are sequential schematic views of the distal end of the medical appliance and introducer apparatus, illustrating the various stages of the introduction method.

DETAILED DESCRIPTION OF THE INVENTION

Figure 4:
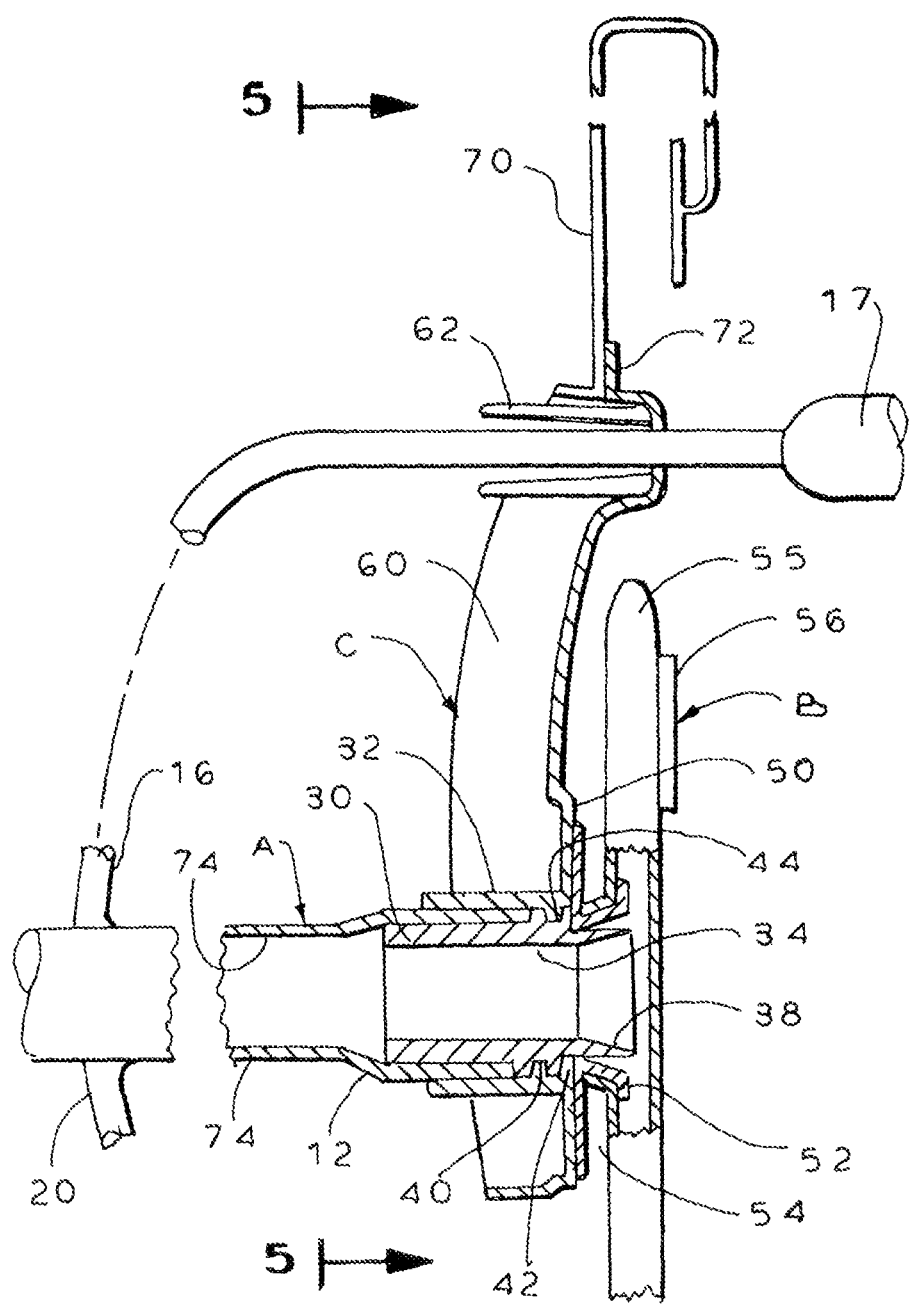
FIG. 4 is a cross-sectional view of the proximal end of the medical appliance.

As seen in FIG. 1, the medical appliance of the present invention includes an elongated flexible tubular element, generally designated A, having a distal end 10 that is designed to be introduced into a body cavity, and a proximal end 12. Element A is preferably approximately 1 meter long and 23 mm in diameter. It collapses to 8 mm in diameter to facilitate passage through the anal sphincter. Element A generally includes a wall 74.

A fecal waste receptacle, generally designated B, is rotatably connected to proximal end 12 of element A, through an adapter plate, generally designated C. Affixed to the exterior surface of the distal end 10 of element A is a low pressure inflatable balloon 14, shown in its deflated state in FIG. 1.

Balloon 14 is inflated with fluid, such as water or saline, through an inflation lumen 16 to a diameter of about 53 mm, with a pressure of less than 26 mm Hg. (0.5 pounds per square inch). Lumen 16 is connected by a Luer valve connector 17 to an inflation fluid source, such as a syringe 18. The syringe is also used to withdraw the inflation fluid, to deflate the balloon.

Preferably, a second, irrigation lumen 20 is also provided. Luman 20 extends to the edge of the distal end 10 of element A and is connected by a Luer valve connector 21 to a source of irrigation fluid, such as a syringe 22. Lumens 16 and 20 are preferably 1 mm to 1.5 mm in diameter.

The distal end 10 of element A and balloon 14 are both made entirely of soft, compliant material so as not to injure any body tissue. That material may be, for example, silicone. Accordingly, the distal end 10 of the appliance itself has insufficient rigidity to permit it to be introduced and correctly positioned within the bowel.

For that reason, separate introducer apparatus, generally designated D, is provided to facilitate introduction and placement of the distal end 10 of element A in the rectum. As explained below, apparatus D is rigid. It is designed to engage distal end 10 of element A and facilitate its introduction into and positioning within the bowel. Apparatus D is then separated from the medical appliance and removed from the body cavity, leaving only the soft, compliant distal end 10 of element A in the body.

As best seen in FIG. 2, balloon 14 surrounds the distal end 10 of appliance A. Preferably, the balloon has a toroidal shape when fully inflated. The wall of the balloon is fabricated in that fully inflated shape, of substantially non-expandable material, such that it cannot be inflated beyond its pre-determined size. As detailed below, the pressure of the fluid within balloon 14 is carefully regulated such that the balloon cannot apply a pressure beyond a pre-determined low level on the surrounding tissue.

As seen in FIG. 3, inflation lumen 16 and irrigation lumen 20 are preferably formed as an integral part of the interior surface of the wall of element A. Each of the lumens 16, 20 has a portion that extends within element A and a portion that extends through an opening 24, 26, respectively, in the wall of element A, for attachment to fluid sources 18, 22, respectively. Preferably, the internal portions of lumens 16 and 20 extend along the entire length of element A. It is then possible to fabricate element A with the external portions of the lumens located at any point along the length of the element.

Inflation lumen 16 has a closed end adjacent the edge of distal end 10 of element A. However, a passage 28 connects lumen 16 with the interior of balloon 14 to permit the inflation fluid, usually water or saline, to be introduced into balloon 14 to inflate the balloon and to be removed from the balloon to deflate the balloon.

Irrigation lumen 20 extends to a point proximate the edge of distal end 10 of element A and has an open end such that the irrigation fluid can be introduced into the bowel. The irrigation fluid is supplied as needed from a source, such as syringe 22.

The balloon inflation system can function in two ways. It can allow the balloon to shrink in volume if the internal pressure increases, maintaining only the desired pressure on tissue, such as by spring loading the syringe plunger to a pre-determined level. Alternatively, the balloon can be fixed in volume once the pressure is reached on insertion. If this is done at a time when the bowel is relaxed, the pressure on tissue will only increase when the bowel is in constriction. As this is only a periodic event, the tissue will be fully profused between constrictions.

The balloon is inflated and the pressure is regulated remotely from the tubular element. The inflation lumen 16 extends from the balloon to the inflation fluid source located outside of the body. The fluid source can be manually operated or can be regulated by an electronic or mechanical system.

In one preferred embodiment, the balloon is operably connected to a fluid reservoir, such as syringe 18. The syringe can be a 50 cubic centimeter commercial polycarbonate Luer lock syringe with a silicone plunger seal and a barrel between 1 to 1.25 inches in diameter. The volume of the syringe can be changed to place the fluid within under pressure that is purely dependent on the force applied on the plunger. Spring loading the plunger of syringe 18 with a spring 19 with the appropriate force will set the internal balloon to the desired pressure. The fluid path to the balloon could then be left open to maintain that pressure or it could be closed by a valve or clamp 23 to maintain the balloon's volume. The pressure within the syringe thus determines the size of the balloon and thus the pressure applied to the tissue.

For accurate pressure measurements, the elastic force of the balloon would have to be taken into consideration. However, the effect of the elasticity of the material of which the balloon is made is minimized if the balloon is fabricated of substantially non-expandable material, in the desired fully inflated shape. Then, the pressure within the balloon would determine the pressure exerted on tissue, up to its pre-determined size.

Where an undersized balloon is used, the balloon would fully be inflated with very little pressure on the tissue. With a closed inflation system, this will be known however, as the volume of fluid used to inflate the balloon can be monitored by, for example, providing syringe 18 with standard markings in single cubic centimeter increments. If the fluid volume required to produce the desired pressure is too great or too small; the balloon is over or undersized. The caregiver would have an indication of this from the fluid volume used to inflate the balloon. If the inflation volume were out of acceptable limits, a different appliance with the correct size balloon would be indicated. The accuracy of the volume measurement within the balloon can be maintained by using an incompressible fluid or by compensation for the pressure increase by the ideal gas law, if a gas is used.

The appliance could be supplied with a pre-filled fluid reservoir that is maintained under a near constant pressure by a resilient mechanical system, for example, a syringe 18 with a plunger between the fluid and a near constant force spring. The spring pressing on the plunger would maintain the fluid at the desired pressure. Once the appliance is inserted into the patient, the valve on clamp 23 would be opened allowing fluid from the syringe to fill and inflate the balloon to the desired pressure. The valve or clamp 23 could be left open to maintain that pressure over time or it could be closed to maintain the fixed volume.

The same components could be supplied without fluid, but with a fluid supply port 25. The caregiver would supply the fluid and supply the pressure to put in a known range of volume of fluid. The syringe plunger backed by the spring 19 would act as a pressure gauge. The caregiver would be instructed to stop injecting fluid once the proper pressure is reached. If the fluid injected is not within the prescribed range, the balloon is the wrong size and must be removed.

Alternatively, the inflation system could include a simple pressure gauge 27 attached to lumen 16 to allow the caregiver to only inflate the device to the target pressure. This configuration requires the system to function in the fixed volume state once the pressure is determined on insertion. It is also possible to fabricate the syringe plunger with the pressure gauge incorporated into it. The plunger stem could contain an integrated or assembled spring that indicates the pressure in the fluid in the syringe barrel. The spring could create a gap between two portions of the plunger stem. As the pressure increases, the spring compresses and the two portions of the plunger move closer together. Scales on the two portions can indicate pressure by their relative position to each other.

Figure 5:
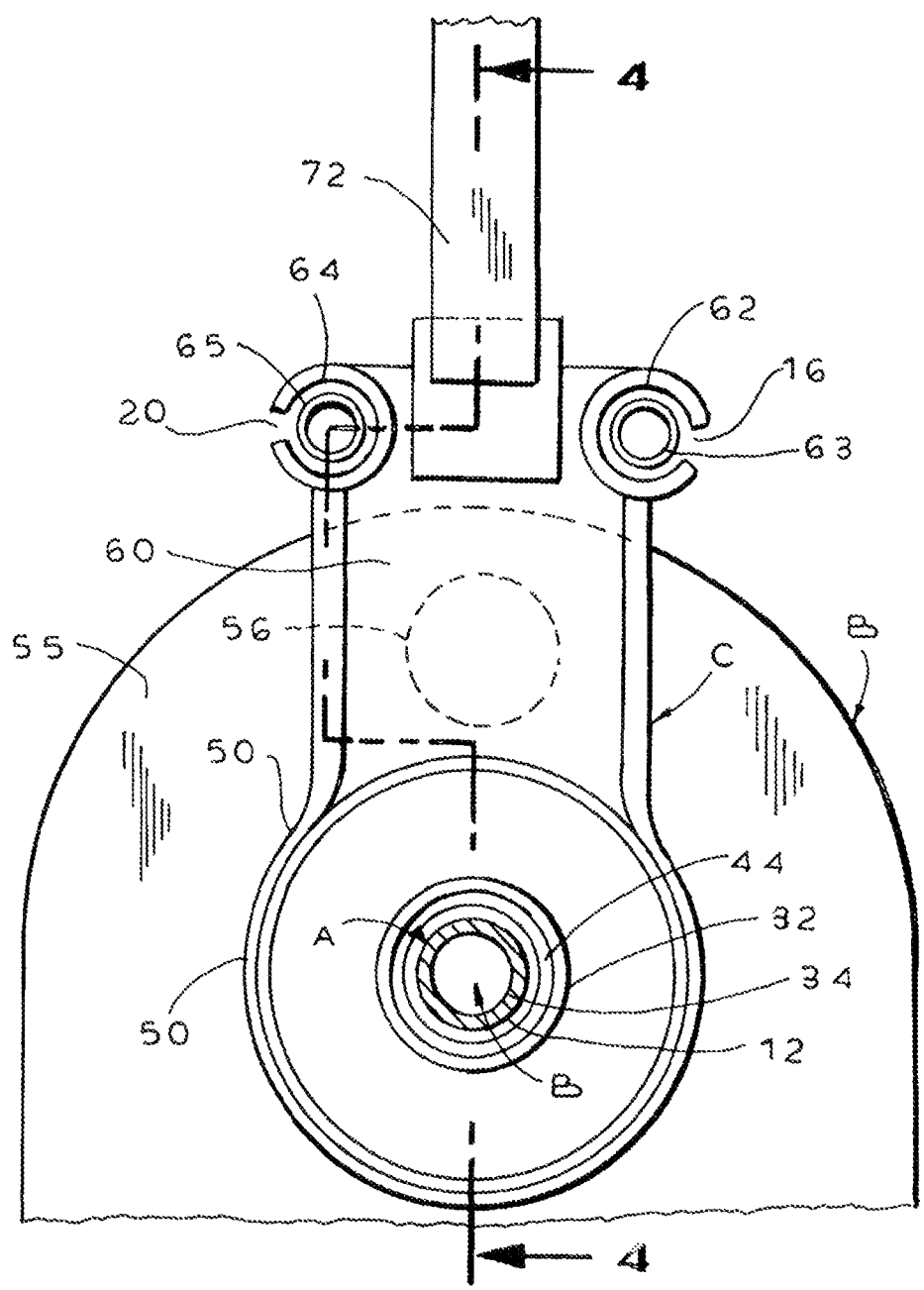
FIG. 5 is a cross-sectional view taken along line 5-5 of FIG. 4.

Referring now to FIGS. 1, 4 and 5, the proximal end 12 of element A is rotatably connected to adapter plate C by first and second parts 30 and 32. Part 30 is generally tubular in shape and has an outer diameter that is substantially equal to or slightly larger than the inner diameter of element A. Proximate end 12 of element A is received over and fixed on one end of part 30.

The other end of part 30 is rotatably received within part 32, which is also generally tubular. However, part 32 has a larger inner diameter than the outer diameter of part 30, plus the thickness of element A, such that even when proximate end 12 of element A is situated on part 30, there is sufficient clearance between the parts to permit rotation.

Part 32 is fixed to plate C and defines a circular opening 34 through plate C, through which the end 38 of part 30 extends. The end 38 of part 30 extends into pouch B to create a waste path from element A to the pouch.

The exterior surface of part 30 has a pair of outwardly extending spaced circumferential surface protrusions 40, 42 defining a circumferential recess or groove 44. The interior surface of part 32 has an inwardly extending annular protrusion 46 which is adapted to be received in groove 44 to permit part 30, and hence proximal end 12 of element A, to be manually rotated relative to part 32 and hence plate C.

Plate C is preferably made of plastic and has a body with a lower, generally circular portion 50 through which opening 34 extends. Part 32 is fixed to one side of portion 50. The other side of portion 50 of plate C carries a first inter-engaging part 52 in the form of an annular protrusion or ring welded to its surface. Part 52 surrounds opening 34 in plate C. Receptacle B preferably takes the form of a standard ostomy pouch 55.

Pouch 55 includes an entrance opening defined by a second inter-engaging part 54, in the form of an annular channel, welded to the pouch wall. Part 52 is detachably received into part 54 in a "snap-fit" fashion.

The contours of inter-engaging parts 52, 54 are shaped so that when the parts are engaged and the pouch is attached to the plate, a fluid tight seal is formed. This seal is strong enough to prevent the weight of the filled pouch from causing accidental attachment of the pouch.

Inter-engaging parts of this type are well known in the art and commonly used in two-piece ostomy appliances. The particular coupling structure preferred for the present invention is disclosed in U.S. Pat. No. 5,693,036 issued on Dec.

2, 1997 to Kilgour entitled: Method Of Injection Moulding An Undercut Formation On A Circular Body And A Closure Assembly Including A Coupling Element, owned by Bristol-Myers Squibb Company of Lawrenceville, N.J.

Pouch 55 preferably has a capacity of 1 to 1.25 liters. It is formed of multiple layers of plastic film welded together. It may include an activated carbon filter 56 for odor control, as is common in ostomy pouches. Filter 56 permits flatus gas to escape from the pouch interior such that pressure does not build up within the pouch. Preferably, the exterior wall of pouch B is transparent and is provided with measurement markings.

The top portion 60 of the body of plate C is substantially rectangular and includes first and second parts 62, 64 with openings 63, 65 respectively adapted to receive inflation lumen 16 and irrigation lumen 20 for stowage. In this manner, the external portions of lumens 16 and 20 can be retained by plate C and will not interfere with the caregiver.

Plate C is designed to hang from a stationary object, such as a bed rail 70. A Velcro strap 72 is provided for that purpose. Strap 72 extends upwardly from portion 60 of plate C and can be closed around bed rail 70, in a conventional manner.

Introducer apparatus D is required to insert distal end 10 of element A into the bowel because the distal end 10 of element A is formed entirely of soft, complaint material. Apparatus D is depicted in FIG. 1 as it appears separately from element A, and in FIG. 6 as it appears engaged with element A. The sequence of how introducer apparatus D is used to engage the distal end 10 of element A and introduce it through the anus or stoma is depicted in FIGS. 7(*a*) through 7(*e*).

Apparatus D consists of two portions. The first portion is a rigid plastic elongated core element 80 consisting of a stiff rod or shaft with a distal end 82. An enlarged cylindrical part 84 is located at its proximal end. The second portion of the apparatus is a soft, complaint silicone sleeve 86. Core 80 is received within sleeve 86. Preferably, part 84 at the proximal end of part core 80 is received within and fixed to the interior surface of the proximal end of sleeve 86. Sleeve 86 is crimped at point 88, adjacent the distal end of core 80. In this manner, core 80 and sleeve 86 are attached together to form a unit.

A section 90 of sleeve 86 extends beyond the distal end 82 of core 80. Section 90 preferably has a length of about 15 mm. However, section 90 can have a length in the range of between half the diameter of the sleeve to several times the sleeve diameter. Section 90 of sleeve 86 is shown in its initial, non-inverted state, in FIGS. 1 and 7(*a*) through 7(*c*). Section 90 is formed so that it can be inverted over the distal end of element A, including balloon 14 in its uninflated condition, to engage element A and compress balloon 14, as seen in FIGS. 6 and 7(*d*).

As seen in FIGS. 7(*b*) and 7(*c*), prior to engaging element A, apparatus D is placed proximate the distal end 10 of element A, with the edge of distal end 10 located below crimp 88. Balloon 14 in its deflated state is wrapped around apparatus D, below crimp 88. Sleeve section 90 is then inverted over end 10 of element A, as seen in FIG. 7(*d*), such that balloon 14 is fully compressed. The distal end 10 of element A, including the compressed balloon, is thus engaged by apparatus D. It should be noted that in this condition, inverted sleeve section 90 forms a soft, rounded tip on apparatus D to facilitate introduction of element A and apparatus D into the bowel.

Once properly positioned within the bowel, the distal end 10 of element A is separated from apparatus D. This can be accomplished by retaining element in position as apparatus D is moved distally to disengage it from element A. Apparatus D may then be withdrawn from the bowel. However, disengagement can also be accomplished by inflation of the balloon. Inflation of balloon 14 will automatically cause sleeve section 90 to return to its non-inverted condition, separating apparatus D from element A, as seen in FIG. 7(*e*). After removal, introducer apparatus D is discarded.

It will now be appreciated that the present invention relates to a medical appliance with an end designed to be introduced into a body cavity that is made entirely of soft, compliant material. That end of the appliance carries an inflatable balloon made of non-expandable material, formed in its fully inflated shape, to prevent overexpansion. The balloon is inflated to a predetermined low pressure level to prevent pressure necrosis on the adjacent tissue.

The present invention also relates to a method and apparatus for introducing the medical appliance into the body cavity. The introducer apparatus includes a rigid core element surrounded by a soft, compliant sleeve, crimped at a location adjacent the distal end of the core element, to form an invertable section. The distal end of the appliance is situated adjacent the apparatus, the balloon is wrapped around the apparatus and the sleeve section is inverted over the appliance, engaging the appliance, compressing the balloon and forming a soft, rounded insertion tip. The unit is then introduced into the body cavity. After the appliance is separated from the apparatus, the apparatus is withdrawn.

While only a single preferred embodiment of the present invention has been disclosed for purposes of illustration, it is obvious that many variations and modifications could be made thereto. It is intended to cover all of these variations and modifications that fall within the scope of the invention, as defined by the following claims:

I claim:

1. A waste management appliance comprising an elongated tubular element having a distal end portion, and a proximal end; an inflatable balloon fixed to and surrounding said distal end portion of said tubular element, said balloon having a planar distal end surface situated in a plane intersecting with said distal end portion of said tubular element, and wherein said balloon is fabricated in a pre-determined fully inflated shape such that said balloon can be expanded to its pre-determined size; an inflation lumen connected to an interior of said balloon so as to permit inflation of said balloon; and a waste collection receptacle connected to said proximal end of said element.

2. A waste management appliance comprising an elongated tubular element having a distal end portion, and a proximal end; an inflatable balloon fixed to and surrounding said distal end portion of said tubular element, said distal end portion of said tubular element and said balloon both being formed entirely of soft, compliant material, and wherein said balloon is fabricated in a pre-determined fully inflated shape such that said balloon can be expanded to its pre-determined size; an inflation lumen connected to an interior of said balloon so as to permit inflation of said balloon; and a waste collection receptacle detachably mounted to said proximal end of said element.

3. The appliance of claim 2, wherein said balloon is toroidal in shape when fully inflated.

4. The appliance of claim 2, wherein said balloon is formed of a non-expandable material.

5. The appliance of claim 2 wherein said balloon is formed of silicone.

6. A waste management appliance comprising an elongated tubular element having a distal end and a proximal end, said distal end surrounded by an inflatable balloon with an externally accessible inflation lumen, and wherein said balloon is fabricated in a pre-determined fully inflated shape such that said balloon can be expanded to its pre-determined size; and a waste collection receptacle detachably connected to the proximal end of the appliance.

7. The appliance of claim 6, wherein said balloon is inflated to a pre-determined maximum pressure.

8. The appliance of claim 6, wherein the balloon is toroidal in shape when fully inflated.

9. The appliance of claim 6, wherein said tubular element comprises a wall and, wherein at least a portion of said inflation lumen is attached to said wall.

10. The appliance of claim 6, wherein said tubular element comprises a wall with an interior surface and wherein at least a portion of said inflation lumen is integral with said interior wall surface.

11. The appliance of claim 6, further comprising an externally accessible irrigation lumen having an end proximate said distal end.

12. The appliance of claim 11, wherein said irrigation lumen extends at least a portion of an entire length of said tubular element.

13. The appliance of claim 6, wherein said tubular element has a wall and wherein said inflation lumen is attached to said wall along at least a portion of an entire length thereof.

14. The appliance of claim 6, wherein said tubular element has a wall with an interior surface and wherein said inflation lumen is attached to said interior wall surface along at least a portion of an entire length of said tubular element.

15. The appliance of claim 6, wherein the inflation lumen is inflated using fluid.

16. The appliance of claim 6, wherein the inflation lumen is inflated using a syringe.

17. The appliance of claim 16, wherein the syringe comprises a plunger and a spring.

18. The appliance of claim 6, wherein the inflation lumen is inflated using a pressure gauge.

19. The appliance of claim 11, wherein the irrigation lumen is an irrigation fluid source.

20. The appliance of claim 6, further comprising a coating of gas and odor barrier material.

* * * * *